US009561294B2

(12) United States Patent
Fuller et al.

(10) Patent No.: US 9,561,294 B2
(45) Date of Patent: *Feb. 7, 2017

(54) EX VIVO ANTIMICROBIAL DEVICES AND METHODS

(71) Applicant: ArgentumCidal Electrics, Inc., State College, PA (US)

(72) Inventors: Thomas A. Fuller, State College, PA (US); Richard Wysk, State College, PA (US); Wayne J. Sebastianelli, Boalsburg, PA (US); Paul H. Cohen, Apex, NC (US); Robert C. Voigt, State College, PA (US)

(73) Assignee: ARGENTUMCIDAL ELECTRICS, INC., State College, PA (US)

( * ) Notice: Subject to any disclaimer, the term of this patent is extended or adjusted under 35 U.S.C. 154(b) by 343 days.

This patent is subject to a terminal disclaimer.

(21) Appl. No.: 14/090,624

(22) Filed: Nov. 26, 2013

(65) Prior Publication Data

US 2014/0286833 A1 Sep. 25, 2014

Related U.S. Application Data

(63) Continuation of application No. 12/005,649, filed on Dec. 27, 2007, now Pat. No. 8,609,036.

(Continued)

(51) Int. Cl.
*A61L 2/03* (2006.01)
*A61L 2/14* (2006.01)
(Continued)

(52) U.S. Cl.
CPC .. *A61L 2/14* (2013.01); *A61L 2/03* (2013.01); *A61L 2/238* (2013.01); *E05B 1/0069* (2013.01)

(58) Field of Classification Search
CPC ............ A61L 2/0011; A61L 2/02; A61L 2/03; A61L 2/232; A61L 2/236
(Continued)

(56) References Cited

U.S. PATENT DOCUMENTS 2,855,922 A 10/1953 Knappwost
3,954,407 A 5/1976 Andary
(Continued)

FOREIGN PATENT DOCUMENTS

WO WO 2004/017738 A1 4/2004

OTHER PUBLICATIONS

Colomano, C. et al., "Activation of Antibacterial Silver Coatings on Surgical Implants by Direct Current: Preliminary Studies in Rabbits," *Am J. Vet. Res.*, Jun. 1980, pp. 964-966, 41(6).

(Continued)

*Primary Examiner* — Timothy Cleveland
(74) *Attorney, Agent, or Firm* — Finnegan, Henderson, Farabow, Garrett & Dunner LLP

(57) ABSTRACT

A method and device for destroying and inhibiting exposure to microbes and infection includes a first element and a second element, and a power source. At least one of the elements includes antimicrobial metal, which, when energized by the power source, produces ions that are lethal to microbes. The device can be incorporated into virtually any useful object. During normal use of the object, electrical communication is established between the two elements, causing current supplied from the power source to flow through the antimicrobial metal. The two elements are configured and arranged to ensure that ions flowing from the antimicrobial metal flow through the region in which it is desired to kill microbes. The antimicrobial metal can be on the surface of the element, incorporated into the material (Continued)

making up the element, or provided in any other way that allows the antimicrobial effect to be achieved.

17 Claims, 8 Drawing Sheets

Related U.S. Application Data

(60) Provisional application No. 60/882,305, filed on Dec. 28, 2006.

(51) Int. Cl.
*A61L 2/238* (2006.01)
*E05B 1/00* (2006.01)

(58) Field of Classification Search
USPC .......................................................... 422/22
See application file for complete search history.

(56) References Cited

U.S. PATENT DOCUMENTS

| | | | |
|---|---|---|---|
| 4,027,393 | A | 6/1977 | Ellis |
| 4,054,139 | A | 10/1977 | Crossley |
| 4,252,525 | A | 2/1981 | Child |
| 4,291,125 | A | 9/1981 | Greatbatch |
| 4,308,859 | A | 1/1982 | Child |
| 4,476,590 | A | 10/1984 | Scales |
| 4,569,673 | A | 2/1986 | Tesi |
| 4,615,705 | A | 10/1986 | Scales et al. |
| 5,100,671 | A | 3/1992 | Maeda |
| 5,322,520 | A | 6/1994 | Milder |
| 5,324,275 | A | 6/1994 | Raad et al. |
| 5,358,514 | A | 10/1994 | Schulman |
| 5,383,935 | A | 1/1995 | Shirkhanzadeh |
| 5,520,664 | A | 5/1996 | Bricault |
| 5,723,014 | A | 3/1998 | Laurent et al. |
| 5,741,224 | A | 4/1998 | Milder et al. |
| 5,759,564 | A | 6/1998 | Milder et al. |
| 5,814,091 | A | 9/1998 | Dahlberg |
| 5,814,094 | A | 9/1998 | Becker et al. |
| 5,817,325 | A | 10/1998 | Sawan et al. |
| 5,984,905 | A | 11/1999 | Dearnaley |
| 6,034,295 | A | 3/2000 | Rehberg |
| 6,087,549 | A | 7/2000 | Flick |
| 6,120,502 | A | 9/2000 | Michelson |
| 6,143,035 | A | 11/2000 | McDowell |
| 6,238,686 | B1 | 5/2001 | Burrell |
| 6,267,590 | B1 | 7/2001 | Barry |
| 6,393,323 | B1 | 5/2002 | Sawan |
| 6,500,165 | B1 | 12/2002 | Frank |
| 6,579,539 | B2 | 6/2003 | Lawson |
| 6,582,715 | B1 | 6/2003 | Barry |
| 6,610,096 | B2 | 8/2003 | MacDonald |
| 6,663,634 | B2 | 12/2003 | Ahrens |
| 6,731,897 | B2 | 5/2004 | Nagano et al. |
| 6,778,861 | B1 | 8/2004 | Liebrecht |
| 7,615,070 | B2 | 11/2009 | Biscup |
| 8,609,036 | B2 * | 12/2013 | Fuller ...................... A61L 2/03 422/22 |
| 2004/0243130 | A1 | 12/2004 | Biscup |
| 2006/0004431 | A1 | 1/2006 | Fuller et al. |
| 2006/0265026 | A1 | 11/2006 | Madjar et al. |
| 2008/0199352 | A1 | 8/2008 | Fuller et al. |
| 2009/0259319 | A1 | 10/2009 | DiSilvestro et al. |
| 2010/0100188 | A1 | 4/2010 | Fuller et al. |
| 2010/0198357 | A1 | 8/2010 | Fuller et al. |

OTHER PUBLICATIONS

Berger, T.J. et al., "Antifungal Properties of Electrically Generated Metallic Ions," *Antimicrobial Agents and Chemotherapy*, Nov. 1976, vol. 10, No. 6, 856-60.

Sudmann, Einar et al., "Systematic and Local Silver Accumulation after Total Hip Replacement using Silver-Impregnated Bone Cement," *Medical Progress Through Technology*, 1994, pp. 179-131, 20(3-4).

Tozzi, Piergiorgio et all, "Silver-Coated Prosthetic Heart Value: A Double-bladed Weapon," *European Journal of Cardio-thoracic Surgery*, 2001, pp. 729-731, No. 19.

Mackeen, Patricia C. et al., "Silver-Coated Nylon Fiber as Antibacterial Agent," *Antimicrobial Agents and Chemotherapy*, Jan. 1987, pp. 93-99, vol. 31, No. 1.

Deitch, Edwin A. et al., "Silver-Nylon: A New Antimicrobial Agent," *Antimicrobial Agents and Chemotherapy*, Mar. 1983, pp. 356-359, vol. 23, No. 3.

Becker, R. et al., "Treatment of Orthopedic Infections with Electrically Generated Silver Ions," *The Journal of Bone and Joint Surgery*, Oct. 1978, pp. 871-881, vol. 60-A, No. 7.

Hall, R. et al., "Inhibitory and Cidal Antimicrobial Actions of Electrically Generated Silver Ions," *J. Oral Maxillofac. Surg.*, Sep. 1987, pp. 779-784, vol. 45(9).

Straub, A.M. et al., "Phase 1 Evaluation of a Local Delivery Device Releasing Silver Ions in periodontal Pockets: Safety, Pharmacokinetics and Bioavailability," *Journal of Periodontal Research*, 2001, pp. 187-193, 36.

Von der Borden, A. et al., "Electric Current-Induced Detachment of *Staphylococcus* Epidermidis Biofilms from Surgical Stainless Steel." *Applied and Environmental Microbiology*, Nov. 2004, pp. 6871-6874, vol. 70, No. 11.

Written Opinion of the ISA in PCT/US07/26379 (2008).

Written Opinion of the ISA issued PCT/US06/26000-PCT Application from which U.S. Appl. No. 11/922,979 (979) entered the National Stage; 979 claims priority to this aoptication (2006).

International Preliminary Report on Patent Issued in PCT/US06/26000-PCT application from which U.S. Appl. No. 13/922,979 (979) entered the National Stage; 979 claims priority to this application (2008).

Written Opinion issued by Intellectual Property Office in Singapore in Singapore Patent Application No. 200718944-2 corresponding to 979 (2009).

Response to Written Opinion Mar. 30, 2009 issued by Intellectual Property Office in Singapore in Singapore Patent Application No. 200718944-2, Aug. 28, 2009 (Corresponding to U.S. Appl. No. 11/922,979).

Written Opinion issued by Intellectual Property Office in Singapore in Singapore Patent Application No. 200718944-2, Dec. 28, 2009.

Response to Written Opinion issued Dec. 28, 2009 by Intellectual Property Office in Singapore Patent Application No. 200718944-2, Sep. 16, 2010.

Office Action issued by U.S. Patent and Trademark Office in U.S. Appl. No. 11/172,138, Aug. 8, 2007.

Response to Office Action (Aug. 8, 2007) issued by U.S. Patent and Trademark Office in U.S. Appl. No. 11/172,138, Feb. 8, 2008.

Office Action issued by U.S. Patent and Trademark Office in U.S. Appl. No. 11/172,138, Dec. 22, 2008.

Response to Office Action (Dec. 22, 2008) issued by U.S. Patent and Trademark Office in U.S. Appl. No. 11/172,138, Jun. 22, 2009.

Office Action issued by U.S. Patent and Trademark Office in U.S. Appl. No. 11/172,138, Jul. 8, 2009.

Office Action issued by U.S. Patent and Trademark in U.S. Appl. No. 11/172,138, Oct. 14, 2009.

International Search Report and Written Opinion issued in PCT/US2007/26379, Sep. 9, 2008 (corresponding to this application).

Response to International Preliminary Report on Patentability issued in PCT/US2007/26379, Sep. 30, 2009.

International Search Report issued in PCT/US2006/02600, Dec. 19, 2006 (corresponding to U.S. Appl. No. 11/922,979).

Publication of PCT/US2006/026000, Publication No. WO/2007/005842, Nov. 1, 2007.

Publication of PCT/US2007/026379, Publication No. WO/2008/082586, Oct. 7, 2008.

First Official Notification by the Israeli Patent Office in Israeli Patent Application No. 188251, "Prophylactic Bactericidal Implant"

(56) References Cited

OTHER PUBLICATIONS in the name of Argentumcidalelectrics, Inc., issued Jul. 21, 2010 including summary (provided by Israeli patent agent prosecuting application).

Beal, Dr., Charles D., "*Silver Ion Therapy for HIV/AIDS and Septicemia,*" Copyright Notice: "Copyright 1999, Life & Health Research Group".

\* cited by examiner

EX VIVO ANTIMICROBIAL DEVICES AND METHODS

CROSS-REFERENCE TO RELATED APPLICATIONS

This application is a continuation of application Ser. No. 12/005,649, filed Dec. 27, 2007 (now allowed), which claims priority to U.S. Provisional Patent Application No. 60/882,305, filed Dec. 28, 2006, the disclosures of which are expressly incorporated herein by reference to their entireties.

REFERENCE TO RELATED APPLICATIONS

This application claims priority to U.S. Provisional Patent Application Ser. No. 60/882,305, filed Dec. 28, 2006, by the inventors named in this application, the entire content of which is incorporated herein by reference.

BACKGROUND OF THE INVENTION

The present invention relates to the prevention of infection and, more particularly, to the provision of methods and devices for inhibiting exposure to microbes and infection.

Changes in modern lifestyle have occurred which would have been almost unimaginable even a century ago. An adverse consequence of some of these changes has been an increased exposure to harmful microbes. For example, travel between continents is a commonplace experience for many individuals. Unfortunately, increased ease of travel facilitates transfer of potentially disease-causing microbes which were historically limited by geography. Another change is the fact that individuals are surviving bacterial infections, which were previously commonly fatal, due to the advent of antibiotics. People are not the only entities that are changing and adapting. Adaptation by microbes, fueled by today's modern antibiotic prescribing practices has resulted in the appearance of many antibiotic-resistant strains.

The combination of increased exposure to harmful microbes and the more frequent encounter with antibiotic-resistant organisms contributes to a continuing need for antibiotic devices and methods. Effective antibiotic devices and methods are required to decrease exposure to microbes during daily activities in public places as well as in private homes. In addition, reduced exposure to microbes is important in medical and dental settings, such as care facilities, treatment rooms, surgical suites and nursing stations.

SUMMARY OF THE INVENTION

Devices and methods are provided for inhibiting exposure to microbes and infection according to the present invention.

The present invention provides an antimicrobial device, including a device body having a first electrically conductive element having a first external surface and a second electrically conductive element having a second external surface, the second element being electrically isolated from said first element, a first metal component containing an antimicrobial metal disposed on the first external surface of the device body, a power source for supplying current to the first metal component, the first and second elements being adapted to being electrically connected to each other by an object external to the antimicrobial device, whereby current flows through the antimicrobial metal causing metal ions to flow from the antimicrobial metal toward the object.

The antimicrobial device can be any object used in everyday life, including those specifically identified hereinbelow.

The present invention also provides a method for inhibiting exposure to microbes and infection. The method includes the steps of providing a device having a device body including an antimicrobial metal having a first external surface and an electrically conductive element having a second external surface, the second element being electrically isolated from the device body, providing a power source for supplying current to the device body, and configuring the device body and the electrically conductive element to cause the device body and the electrically conductive element to be electrically connected to each other by an object external to the antimicrobial device when the device is in normal use, whereby current flows through the antimicrobial metal causing metal ions to flow from the antimicrobial metal toward the object.

DETAILED DESCRIPTION OF THE PREFERRED EMBODIMENTS

Figure 1:
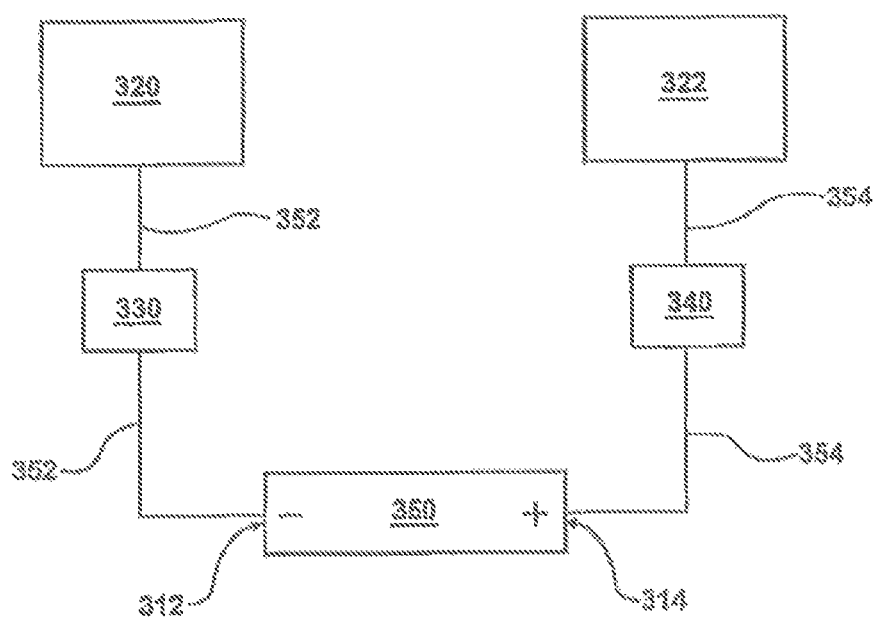
FIG. 1 is a schematic circuit diagram of at least a portion of an electrical circuit included in a device provided by the present invention.

Broadly described, a device for inhibiting exposure to microbes and infection according to the present invention includes at least two portions, described herein as a first element and a second element. Each of these portions has an external surface. At least a first antimicrobial metal component is disposed on the external surface of the first element. Optionally, a second antimicrobial metal component is disposed on the external surface of the second element.

A power source powers a device according to the present invention. Such a power source may be any suitable power source, illustratively including line current or an electrical cell such as an electrochemical cell or a solar cell. Examples include a battery, a capacitor, and connection to external AC. One terminal of the power source is in electrical communication with the first element and the first antimicrobial metal component. The second terminal of the power source is in electrical communication with at least the second element and optionally with the second antimicrobial metal component, if present.

The first and second elements and the first and second antimicrobial metal components are electrically insulated from each other by at least one insulator. The insulator prevents current flow from the first element and/or first antimicrobial metal component to the second element and/or second antimicrobial metal component without completing a circuit through at least the first antimicrobial metal component and an electrical conductor in contact with the surface of the device.

Optionally included in electrical communication with a device according to the present invention is circuitry adapted to modulate a current from the power source. For example, a resistor, a switch, a signal receiver, a relay, a signal transmitter, transformer, a sensor, or a combination of these or other such components and connectors may be included, optionally configured as a circuit board arrangement. In a preferred embodiment, all or part of the circuitry adapted to modulate an electrical current is housed in a cavity in one or more portions of the device.

A metal component includes an antimicrobial metal. An antimicrobial metal is one which inhibits one or more microbes, such as bacteria, protozoa, viruses, and fungi. An antimicrobial metal may be microbiocidal or microbiostatic.

Antimicrobial metals include transition metals and metals in columns 10-14 of the periodic table. Such metals illustratively include silver, gold, zinc, copper, cadmium, cobalt, nickel, platinum, palladium, manganese, and chromium. In certain embodiments, lead and/or mercury may be included in amounts not significantly toxic to a user. Highly preferred is a metal component containing an antimicrobial metal which generates metal ions in response to application of current to the metal component.

A metal component contains an amount of an antimicrobial metal, the amount in the range of 1%-100% by weight of the total composition of the metal component, although in particular embodiments, lower amounts may be included. In general, a metal component included in an inventive device contains an amount of an antimicrobial metal in the range of about 1 nanogram to about 1 kilogram. A metal component preferably contains at least 50 percent by weight of an antimicrobial metal, further preferably contains at least 75 percent by weight of an antimicrobial metal and still further preferably contains at least 95 percent by weight of an antimicrobial metal. In another preferred embodiment, the metal component is substantially all antimicrobial metal. In particular, the metal component is capable of releasing a metal ion when an electrical current is applied to the metal component.

Materials other than an antimicrobial metal may also be included in a metal component. For instance, a metal component may further include metals which are non-antimicrobial in one configuration according to the invention, for instance to provide structural support and lower cost of the metal component. In an alternative embodiment, a non-metal constituent is included in the metal component, for instance to provide structural support and lower cost of the metal component. Exemplary non-metal constituents include such substances as inorganic and organic polymers, and biodegradable materials. A non-metal constituent or non-antimicrobial metal included in a metal component may be biocompatible. Preferably, the metal component is electrically conductive.

A metal component may be provided in any of various forms, illustratively including, a substantially pure metal, an alloy, a composite, a mixture, and a metal colloid. Thus, in one embodiment, a metal component is a substance doped with an antimicrobial metal. For instance, in a particular example, a stainless steel and/or titanium alloy including an antimicrobial metal may be included in a metal component.

By example, the antimicrobial properties of silver are particularly well-characterized and a metal component preferably contains an amount of silver, the amount in the range of 1 percent-100 percent by weight of the total composition of the metal component, although lower amounts may be included in particular embodiments. A metal component preferably contains at least 50 percent by weight of silver, further preferably contains at least 75 percent by weight silver and still further preferably contains at least 95 percent by weight silver. In another preferred embodiment, the metal component is substantially all silver.

Copper is also a preferred metal included in a metal component and a metal component preferably contains an amount of copper in the range of 1%-100% by weight of the total composition of the metal component, although lower amounts may be included in particular embodiments. In one embodiment, at least 50% by weight copper is included, further preferably a metal component contains at least 75% by weight copper and still further preferably contains at least 95% by weight copper. In another preferred embodiment, the metal component is substantially all copper. In particular, the metal component is capable of releasing a metal ion when an electrical current is applied to the metal component.

A combination of metals is also contemplated as included in a metal component. In some instances, certain metals may be more effective at inhibiting growth and/or killing particular species or types of bacteria. For example, particular metals are more effective at inhibiting growth and/or killing Gram positive bacteria, while other metals are more effective against Gram negative bacteria as exemplified in the Examples described herein.

In a particular embodiment, both silver and copper are included in a metal component. A combination of silver and copper may provide a synergistic antimicrobial effect. For instance, a lesser amount of each individual metal may be needed when a combination is used. Additionally, a shorter time during which the device is activated may be indicated where a synergistic effect is observed, allowing for conservation of a power source. The ratio of copper to silver in a metal component may range from 1000:1-1:1000. In one embodiment, a metal component preferably contains an amount of a copper/silver combination in the range of 1-100 percent by weight of the total composition of the metal component, although lower amounts may be included in particular embodiments. In one embodiment, at least 50 percent by weight of a copper/silver combination is included, further preferably a metal component contains at least 75 percent by weight of a copper/silver combination and still further preferably contains at least 95 percent by weight of a copper and silver in combination. In another preferred embodiment, the metal component is substantially all copper and silver.

In a further preferred embodiment, a metal which has antimicrobial properties but which does not have increased antimicrobial properties when an electrical current is applied to the metal is included in a metal component. For example, cadmium has antimicrobial properties effective against a wide range of microbes, as described in the Examples, and which are not increased by application of an electrical current. Such a metal is optionally included in a metal component along with one or more metals capable of releasing a metal ion when an electrical current is applied to the metal component. In particularly preferred embodiments, cadmium and silver, cadmium and copper, or cadmium, silver and copper are included in a metal component. The ratio of one or more metals capable of releasing a metal ion when an electrical current is applied to the metal component to one or more metals whose antimicrobial activity is not increased when an electrical current is applied in a metal component may range from about 1000:1-1:1000. In one embodiment, a metal component preferably contains an amount of a copper and/or silver and an amount of cadmium such that the ratio of copper and/or silver to cadmium is in the range of about 1000:1-1:1000. A combination of silver and/or copper and cadmium in a metal component is in an amount in the range of about 1-100 percent by weight of the total composition of the metal component, although lower amounts may be included in particular embodiments. In one embodiment, at least 50 percent by weight of a copper and/or silver and cadmium combination is included, further preferably a metal component contains at least 75 percent by weight of a copper and/or silver and cadmium combination and still further preferably contains at least 95 percent by weight of copper and/or silver and cadmium in combination. In another preferred embodiment, the metal component is substantially all copper and/or silver and cadmium. These and other combinations of antimicrobial metals in a metal component allow for tailoring a device to a specific situation depending on such factors as likelihood of presence of particular microbe type for example.

In a preferred embodiment, the metal component is in the form of a coating disposed on the external surface of the device. The coating can be applied by any of various methods illustratively including dunk coating, thin film deposition, vapor deposition, and electroplating. The metal component in the form of a coating ranges in thickness between $1 \times 10^{-9}$-$5 \times 10^{-3}$ meters, inclusive, preferably $1 \times 10^{-7}$-$4 \times 10^{-3}$ meters, inclusive, and more preferably between $0.5 \times 10^{-6}$-$5 \times 10^{-4}$ meters in thickness.

It is appreciated that, in the context of preferred embodiments of a device or system according to the present invention including at least two elements of a device, each element having a metal component, wherein the metal components are electrically isolated by an insulator, that each element optionally includes a metal component in the form of a metal-containing coating. In this context, the metal-containing coating on the one or more elements of the device is preferably present on at least 50 percent of the external surface of one or both elements of the device. More preferably the metal-containing coating on the one or more elements of the device is preferably present on at least 75 percent of the external surface of one or both elements of the device, and further preferably the metal-containing coating on the one or more elements of the device is preferably present on substantially all of the external surface of the one or more elements of the device. However, an insulator disposed in a current path between the metal containing coating on the surface of the one or more elements electrically insulates one element from another and thus does not include a metal-containing coating in electrical communication with a metal-containing component on the one or more elements of the device.

A coating may be disposed on a surface of a device in a patterned fashion. For example, interlocking stripes of a metal component and an insulator may be arranged on a surface of a device. Such a pattern is preferably designed to inhibit microbes in a continuous region on or near an inventive device. Thus, the distance between discontinuous regions of a coating is selected to account for the diffusion distance of ions generated from an antibacterial coating in response to an applied electrical current. Typically, ions diffuse a distance in the range of about 1-10 millimeters, but diffusion is dependent upon the medium through which the ion will travel.

A metal coating on an element of a device is preferably disposed on an external surface as a single continuous expanse of the coating material.

Optionally, the metal component is in the form of a wire, paint, ribbon, or foil disposed on the external surface of a device. Such a metal component may be attached to the device by welding, by an adhesive, or the like.

In another embodiment, the device may include an antimicrobial metal such that the device or portion thereof is the metal component. A second metal component may be further included in contact with such a device. Thus, for example, a device or portion thereof may include an alloy of stainless steel and an antimicrobial metal, and/or an alloy of titanium and an antimicrobial metal. A commercial example of such a material is stainless steel ASTM grade 30430 which includes 3% copper.

In a further embodiment, a device made of a material including an antimicrobial metal may be formulated such that the antimicrobial metal is distributed non-uniformly throughout the device. For instance, the antimicrobial metal may be localized such that a greater proportion of the antimicrobial metal is found at or near one or more surfaces of the device.

FIG. 1 illustrates a schematic circuit diagram of at least a portion of an electrical circuit included in a device according to the present invention. A first metal component disposed in electrical connection with a first element of an ex vivo device is shown at 320 and a second metal component disposed in electrical connection with a second element of an ex vivo device is shown at 322. Each of the metal components 320 and 322 is in electrical communication with a power source 350. As shown in FIG. 1, the first metal component 320 is in electrical communication with a first terminal 312 of the power source 350 and the second metal component 322 is in electrical communication with a second terminal 314 of the power source 350. Conduits 352 and 354 illustrate electrical connectors between the first and second metal components 320 and 322 and the first and second terminals 312 and 314, respectively, of the power source. Also illustrated are an optional resistor 330 and an optional switch 340, each in electrical communication with the power source. It is noted that the first and second metal components 320 and 322 are not in electrical contact except via the path 352-350-354. In use, an antimicrobial device according to embodiments of the present invention has first and second metal components 320 and 322 connected via an electrical conductor. In particular embodiments, an electrical conductor is not an integral part of an inventive device, the electrical conductor is a microbe, the hand of a user, environmental humidity or other such conductor.

In an alternative embodiment, one element, either 320 or 322, has a potential charge relative to the other element. When one of the elements, either 320 or 322 is brought into contact with an object that is relatively neutral or opposite in charge with respect to the non-contacted element, the charge is dissipated into the object, providing an antimicrobial effect.

An antimicrobial device may be any of various devices which may be broadly described as having a surface likely to harbor undesirable microbes which may then be transferred to an individual who comes in contact with the surface, directly or indirectly. Such devices include clothing; bed linens, towels, filter masks intended to be worn by a human; medical equipment, such as a stethoscope, an endoscope or probe; handheld devices, such as a remote control for an electronic device, a PDA, a headset, an earpiece, a portable or non-portable telephone and a pager; processing equipment for consumables such as foods and drugs, such as a meat grinder, a mixer, a food container, and a utensil; ventilation systems and parts therefore, such as an air handler or an air filter; and dispensers of various types, illustratively including a tissue dispenser and a paper towel dispenser. Further embodiments include surfaces such as a food preparation surface in a kitchen, an examination table used by a physician or veterinarian, a laboratory bench, a bathroom surface such as a sink, toilet, bathtub or shower surface, a bathroom accessory, such as a shower or bathmat, a drain cover, and a toilet brush. Additional embodiments include personal care accessories, illustratively including a toothbrush, and a hairbrush or comb. Hardware devices are provided according to the present invention, illustratively including a doorknob or door handle, a hand railing, a drinking fountain actuator, bathroom hardware and a vehicle steering wheel.

Figure 2:
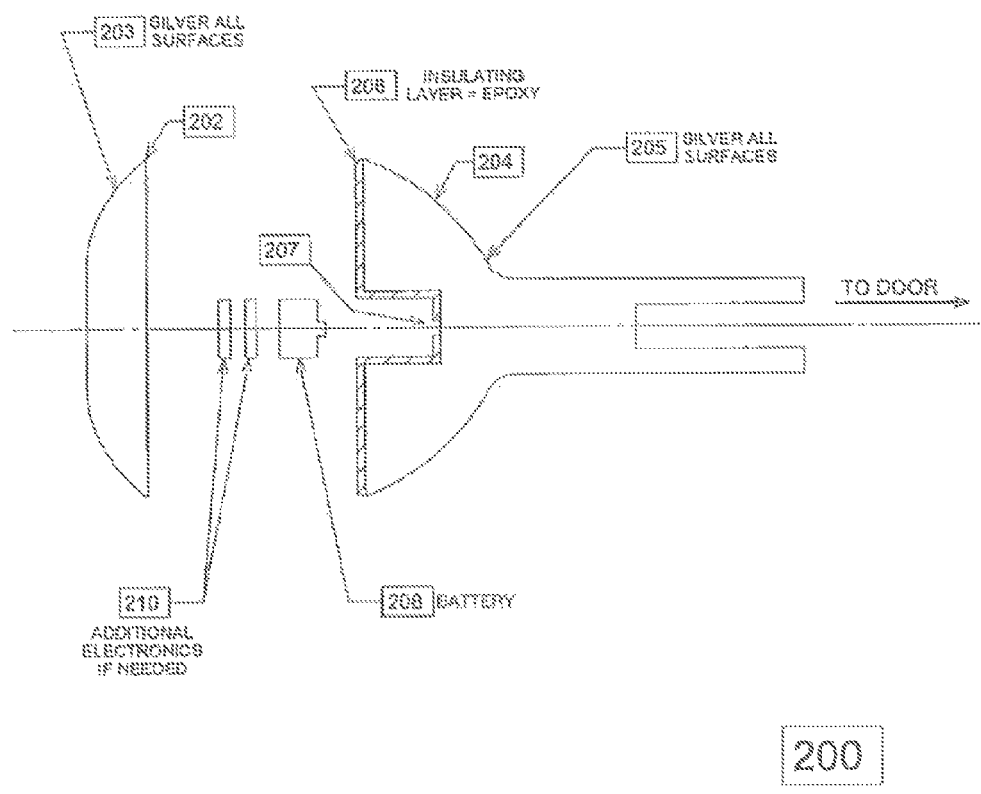
FIG. 2 is a view of an embodiment of an antimicrobial doorknob device provided by the present invention.

FIG. 2 illustrates an embodiment of an antimicrobial doorknob device 200 according to the present invention. An embodiment of an inventive antimicrobial doorknob includes at least two portions, a first element 202 and a second element 204, each element having an external surface. A first antimicrobial metal component 203 is illustrated disposed on the external surface of the first element 202. A second antimicrobial metal component 205 is illustrated disposed on the external surface of the second element 204.

An internal power source is included in the illustrated embodiment, in the form of an electrochemical cell, at 208. The power source 208 is disposed in an internal cavity 207 formed in the second element 204. One terminal of the power source is in electrical communication with the first element 202 and the first antimicrobial metal component 203. The second terminal of the power source is in electrical communication with the second element 204 and the second antimicrobial metal component 205.

An insulator 206 is shown which prevents current flow from the first element 202 and/or first antimicrobial metal component 203 to the second element 204 and/or second antimicrobial metal component 205 without completing a circuit through the first antimicrobial metal component 203, the second antimicrobial metal component and an electrical conductor in contact with the surface of the device (not shown). It is noted that resistive value of the insulator 206 is greater than the resistive value of the hand or other such electrical conductor that completes the circuit 203 to 205 when touching the doorknob.

An electrical conductor in contact with the surface of the device which completes the electrical circuit may be any suitable electrical conductor. The completion of the circuit allows for current-induced release of antimicrobial metal ions from the one or more antimicrobial metal components.

In one embodiment, an electrical conductor comes into contact with an inventive device during normal use. For example, in the context of an antimicrobial doorknob, a human hand may serve as an electrical conductor which completes the circuit. Released antimicrobial ions inhibit growth of microbes transferred from a human hand to a doorknob in regular use and also inhibit transfer of microbes from the doorknob to a hand.

In a further example, a food preparation surface comes into contact with an electrical conductor in the form of a food or moisture in the course of regular use of the food preparation surface. Thus, in an embodiment of the present invention in the form of a food preparation surface is configured such that a food completes the circuit during use of the surface.

In another embodiment, an electrical conductor may be applied to complete the circuit at a desired time. For example, an electrical conductor may be applied at the end of a work period and prior to the beginning of the next work period. In an illustrative example, such an electrical conductor is optionally a conductive blanket used to cover a work surface such as a work table or counter at the end of a work day or during periods of non-use.

Figure 5:
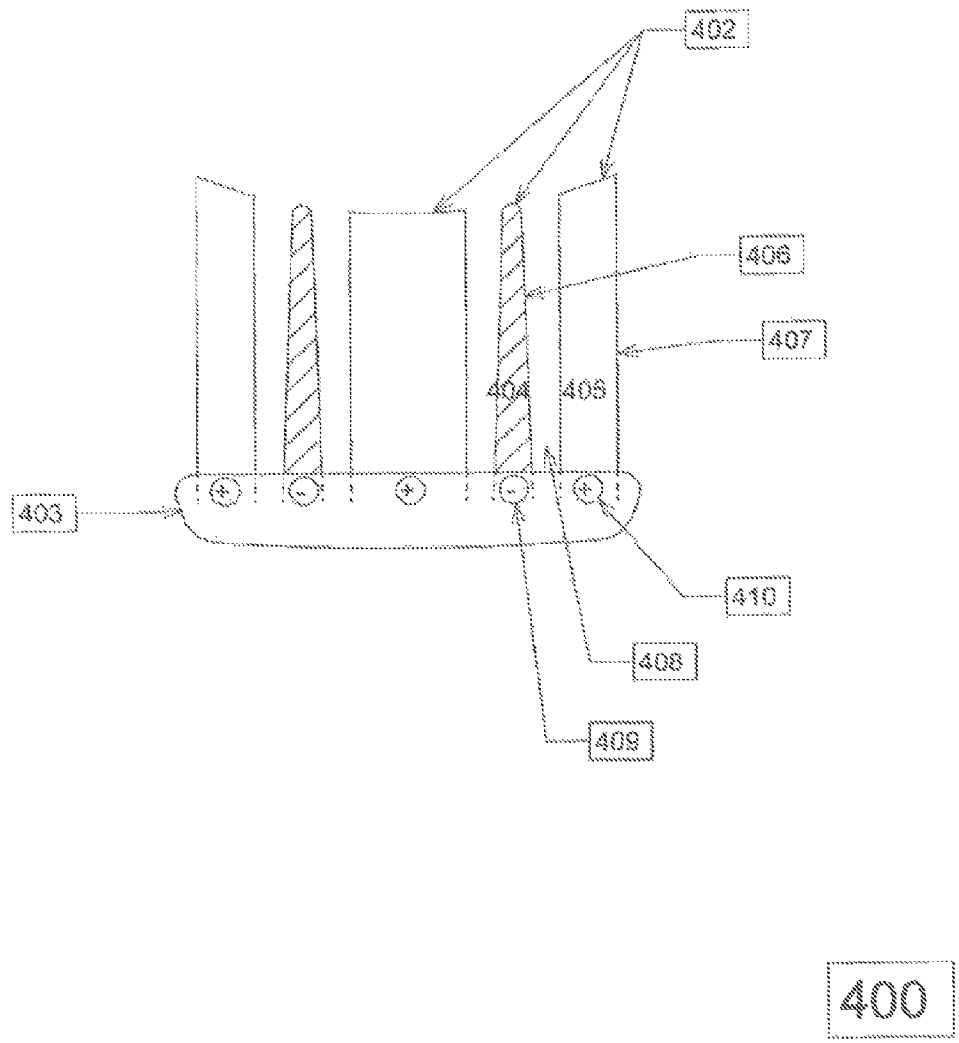
FIG. 5 is a cross-sectional view of a portion of a further embodiment provided by the present invention.

A device according to an embodiment of the present invention includes first and second elements protruding from a base, such as a toothbrush, bathmat, hairbrush, and comb. FIG. 5 illustrates a cross-section of a portion of one such embodiment 400 showing protrusions 402 extending from a base 403. A first antimicrobial metal component 406 is illustrated disposed on the external surface of the first element 404. A second antimicrobial metal component 407 is illustrated disposed on the external surface of the second element 405.

A power source (not shown) is connected to the device 400 such that one terminal of the power source is in electrical communication with the first element 404 and the first antimicrobial metal component 406. The second terminal of the power source is in electrical communication with the second element 405 and the second antimicrobial metal component 407. For example, the terminals may be connected by wires such as shown at 409 and 410.

An insulator 408 is shown which prevents current flow from the first element 404 and/or first antimicrobial metal component 406 to the second element 405 and/or second antimicrobial metal component 407 without completing a circuit through the first antimicrobial metal component, the second antimicrobial metal component and an electrical conductor in contact with the surface of the device (not shown). In the embodiment shown in FIG. 5, an insulator is an air space 408. Additionally, the base 403 is configured so as to prevent flow of current from 404/406 to 405/407 without completing a circuit through the first antimicrobial metal component, the second antimicrobial metal component and an electrical conductor in contact with the surface of the device. An electrical conductor completing the circuit is illustratively a liquid or gel used in tooth cleaning, such as saliva, toothpaste and/or water, a body part contacting the device, such as a human hand, foot and/or scalp.

Figure 6:
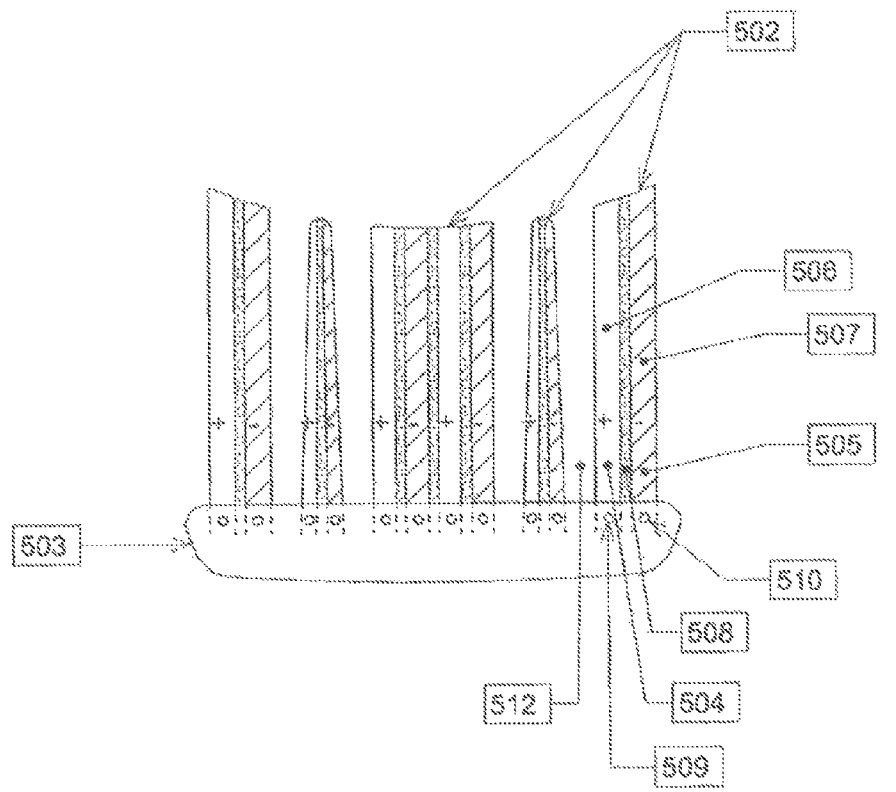
FIG. 6 is a cross-sectional view of a portion of a further embodiment provided by the present invention.

FIG. 6 illustrates a cross-section of a portion of a further embodiment of a device 500 according to an embodiment of the present invention including multiple protrusions 502 extending from a base 503. The protrusions 502 shown include a first antimicrobial metal component 506 is illustrated disposed on the external surface of the first element 504. A second antimicrobial metal component 507 is illustrated disposed on the external surface of the second element 505.

A power source (not shown) is connected to the device 500 such that one terminal of the power source is in electrical communication with the first element 504 and the first antimicrobial metal component 506. The second terminal of the power source is in electrical communication with the second element 505 and the second antimicrobial metal component 507. For example, the terminals may be connected by wires such as shown at 509 and 510.

An insulator 508 is shown which prevents current flow from the first element 504 and/or first antimicrobial metal component 506 to the second element 505 and/or second antimicrobial metal component 507 without completing a circuit through the first antimicrobial metal component, the second antimicrobial metal component and an electrical conductor in contact with the surface of the device (not shown). In an embodiment shown in FIG. 6, a further insulator is an air space 512. Additionally, the base 503 is configured so as to prevent flow of current from 504/506 to 505/507 without completing a circuit through the first antimicrobial metal component, the second antimicrobial metal component and an electrical conductor in contact with the surface of the device. An electrical conductor completing the circuit is illustratively a liquid or gel used in tooth cleaning, such as saliva, toothpaste and/or water, a body part contacting the device, such as a human hand, foot and/or scalp.

Figure 7:
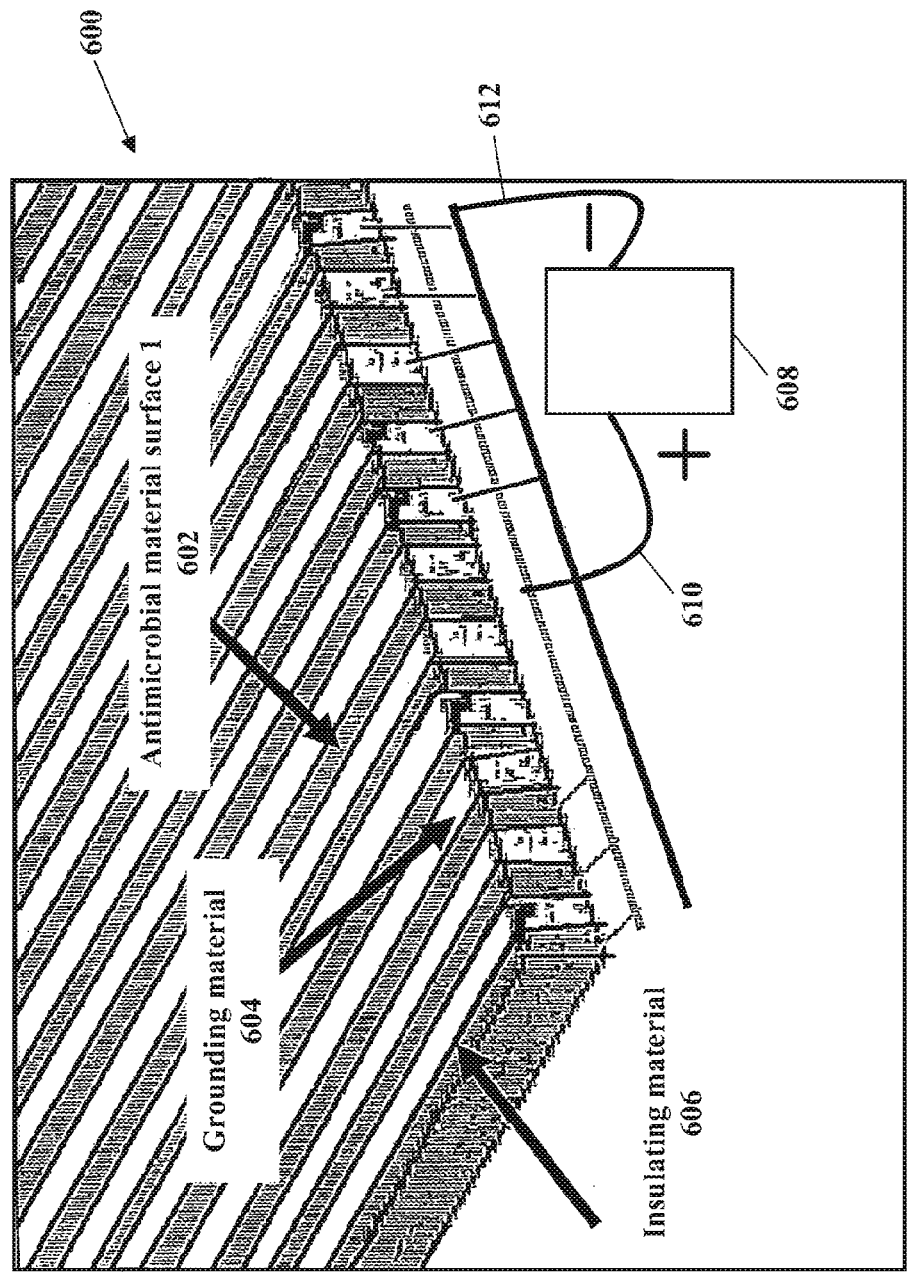
FIG. 7 shows a further embodiment provided by the present invention.

FIG. 7 illustrates an embodiment of an inventive device 600. A device 600 provides a surface which can be incorporated in various devices for antimicrobial effect illustratively including fabric-based article such as an article of clothing, a towel, and/or bed linens such as sheets and blankets; a filter mask; an item of medical equipment; a handheld electronic device; an item of processing equipment for a consumable; a ventilation system component; a wipe dispenser; a food preparation surface; an examination table for a human or an animal; a laboratory bench; a bathroom surface; a bathroom accessory; a personal care accessory; and a hardware apparatus. An inventive device 600 includes a plurality of antimicrobial metal components disposed on the external surface of a plurality of first elements 602, and a plurality of second elements 604, labeled "grounding material." Optionally, a plurality of second antimicrobial metal components is disposed on the external surface of at least one of the plurality of second elements.

Each of the individual first and second elements are separated by an insulator 606. The size of the insulator and thus the size of the separation between an individual first element and an individual second element is selected to optimize an antimicrobial effect. In general, an insulator is dimensioned such that an individual first element and an individual second element are separated by about 0.1 micron-10 cm, inclusive, although not limited to this range of sizes.

A power source 608 is connected to the device 600 such that one terminal of the power source is in electrical communication with the plurality of first elements and the plurality of first antimicrobial metal components. The second terminal of the power source is in electrical communication with the plurality of second elements.

In a further embodiment, an antimicrobial device is provided which includes a device body having a first element having a first external surface and a second element having a second external surface, a first metal component containing an antimicrobial metal disposed on the first external surface of the device body, a power source having a first terminal and a second terminal, the first terminal in electrical communication with the first metal component; and an insulator placed in a current path between the first terminal of the power source and the second terminal of the power source preventing current flowing from the first terminal from reaching the second terminal, wherein activation of the power source creates a potential between the first element and the second element such that placement of an object in contact with the antimicrobial metal results in movement of metal ions from the antimicrobial metal toward the object.

Figure 8:
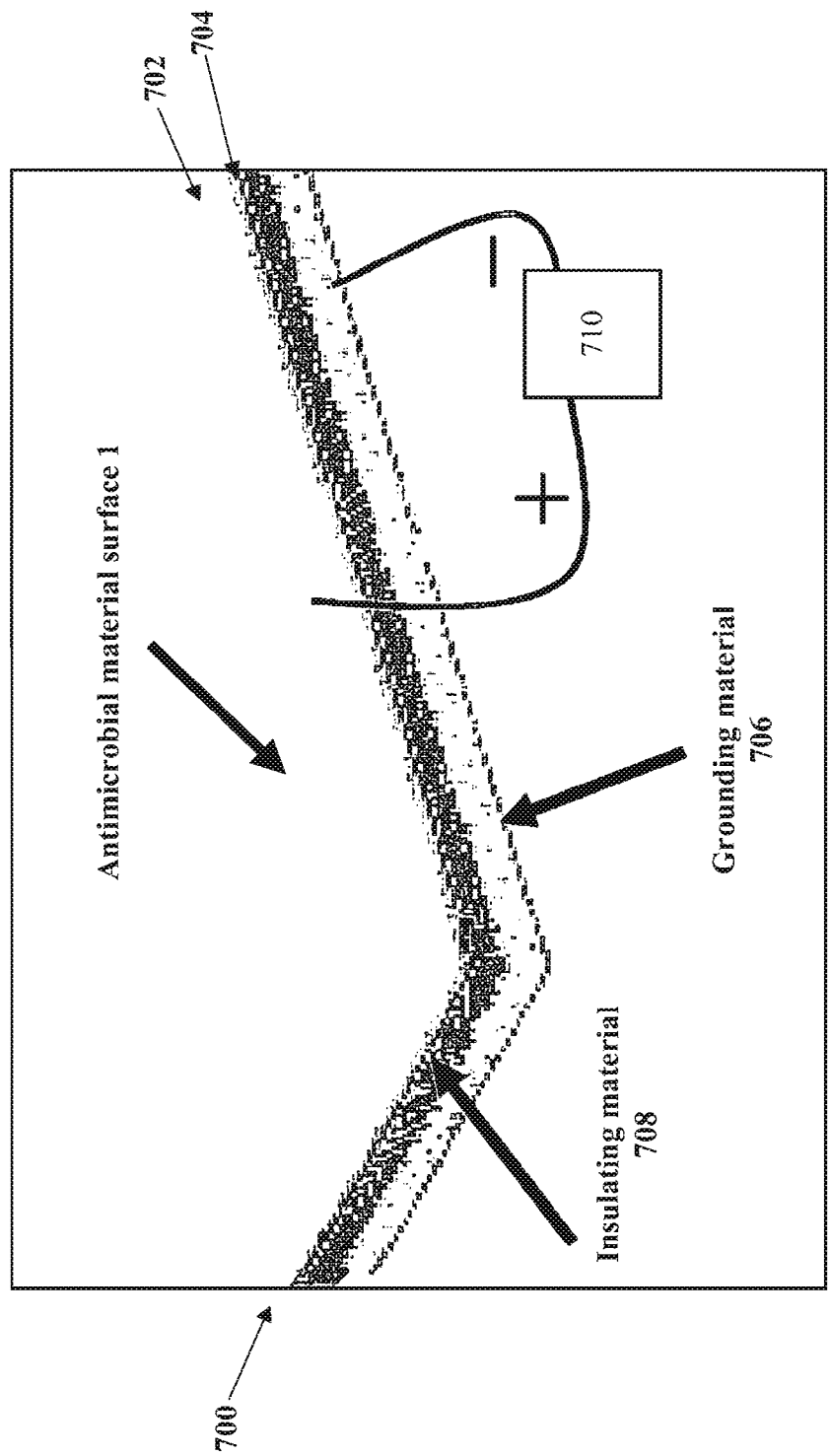
FIG. 8 shows a further embodiment provided by the present invention.

An exemplary embodiment of such an inventive device 700 is shown in FIG. 8. An antimicrobial device 700 includes an antimicrobial metal component disposed on the external surface 702 of a first element 704. As described above, a first element and/or second element is optionally fabricated partially or wholly from an antimicrobial metal. A second element, 706, labeled "grounding material," is depicted and the first and second elements, 704 and 706, respectively, are separated by an insulator 708, labeled "insulating material" in FIG. 8. The size of the insulator and thus the size of the separation between the first element and the second element is selected to optimize an antimicrobial effect. In general, an insulator is dimensioned such that an individual first element and an individual second element are separated by about 0.1 micron-10 cm, inclusive, although not limited to this range of sizes.

A power source 710 is connected to the device 700 such that one terminal of the power source is in electrical communication with the first element and the first antimicrobial metal component. The second terminal of the power source is in electrical communication with the second element.

A device according to the present invention is optionally directly grounded or may use a "floating" ground.

In an embodiment such as shown in FIG. 8, a potential is created between the antimicrobial metal 702 and the second element 706. When an object, not shown, which is neutral or negatively charged with respect to the surface 702 is placed in contact with the surface 702, metal ions from the antimicrobial metal move towards the object, providing an antimicrobial effect. It is noted that a circuit is not completed by the object in an embodiment as illustrated in FIG. 8. The object is illustratively an object typically used in conjunction with the device or which otherwise comes in contact with the device. For example, where the device 700 is incorporated in a food preparation surface, the object is illustratively a food item, a utensil, a user's hand and/or a microbe. A device 700 is optionally incorporated in antimicrobial devices of various types, illustratively including a fabric-based article such as an article of clothing, bed linens, and/or a towel; a filter mask; an item of medical equipment; a handheld electronic device; an item of processing equipment for a consumable; a ventilation system component; a wipe dispenser; a food preparation surface; an examination table for a human or an animal; a laboratory bench; a bathroom surface; a bathroom accessory; a personal care accessory; and/or a hardware apparatus.

Figure 9:
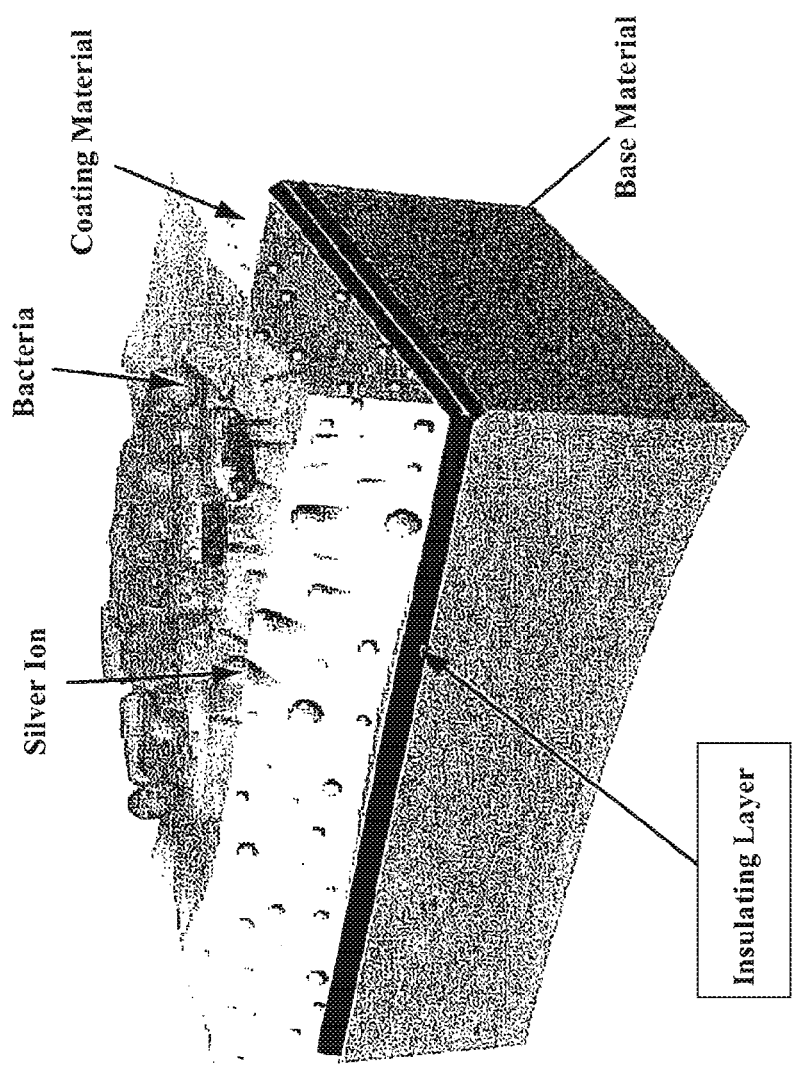
FIG. 9 shows a further embodiment provided by the present invention.

FIG. 9 illustrates an embodiment including a first component including an antimicrobial metal in the form of a "coating material," a second component labeled "base material" and an insulator labeled "insulating layer" disposed between the coating material and base material. FIG. 9 graphically illustrates silver ions moving towards bacteria in contact with the first component, the silver ions providing an antimicrobial effect on the bacteria.

Embodiments of inventive compositions and methods are illustrated in the following examples. These examples are provided for illustrative purposes and are not considered limitations on the scope of inventive compositions and methods.

Example 1

Procedures to identify an antimicrobial metal composition for use in an included metal component may include an examination of each metal's antimicrobial potential using a panel of common Gram (+) and Gram (−) bacterial, fungal species or other microbes. a method adapted from the Kirby Bauer agar gel diffusion technique, the antimicrobial efficacy of eight metals: silver, copper, titanium, gold, cadmium, nickel, zinc and stainless steel AISI 316L and their electrically generated ionic forms are tested against 5 bacterial species and one fungus.

Strains of *Esherichia coli*, *S. aureus*, *Pseudomonas aeruginosa*, *Enterococcus faecalis*, Methicillin resistant *S. aureus* (MRSA), and *Candida albicans* isolated from samples submitted to the Pennsylvania State University Animal Diagnostic Laboratory (*E. coli*, *S. aureus*, *P. aeruginosa* and *E. faecalis*) or J.C. Blair Hospital, Huntingdon, Pa. (MRSA and *C. albicans*), are diluted to a 0.5 MacFarland standard and inoculated onto Mueller-Hinton agar plates (Remel, Lenexa, Kans.).

Metallic wires served as the ion source, specifically: silver (99.97% purity), copper (99.95+% purity), titanium (99.8% purity), gold (99.99% purity), cadmium (99.999% purity), nickel (99.98% purity), zinc (99.999% purity) and stainless steel AISI 316L. All wires are of uniform equal diameter (1.0 mm).

Small holes are burned into opposite sides of the Petri plates which allowed for the aseptic threading of 32 mm lengths of test wire into the agar. Once embedded, 1 cm2 of wire surface area is exposed to the growing microbes.

Electrical currents are generated by placing a standard 1.55 Volt AA battery in series with one of the following resistors: 3.01 MΩ, 1.5 MΩ, 150 kΩ, and 75 kΩ. A 70 mm length of each of the test metals is connected in series with the given resistor. The current that is generated by each of the four different resistors (3.01 MΩ, 1.5 MΩ, 150 kΩ, and 75 kΩ) is 0.5 µA, 1.0 µA, 10 µA, and 20 µA respectively. The 20 µA/cm2 surface area charge is proven in 1974 to be a safe electrical exposure value for the cells. (Barrnco 1974) As calculated with Faraday's equation, a 20 µA/cm$^2$ surface area charge density produced over 80 µg/hour of silver ions.

The circuit is completed by aseptically threading the anode through the opposite hole and embedding it into the agar. One control plate for each microbial species is aseptically threaded with wires, but received no electrical current. The plates are incubated in ambient air at 37° C. for 24 hours, and subsequently examined for bacterial growth and/or zones of inhibition.

Of the eight metals and metal ions tested, silver ions and cadmium show bactericidal efficacy against all bacterial species tested, and copper ions showed bactericidal efficacy against Gram-positive bacteria. Titanium, gold, nickel, zinc and stainless steel AISI had no significant effects in this example.

Exemplary results are shown in Table 1 in which numbers represent measurements of the diameter of the zone of inhibition in millimeters around the central wire. The table shows that silver has some microbiocidal properties when not electrically ionized, since *E. coli* is inhibited by non-charged silver. A smaller current produced results similar to larger currents, and in all cases the addition of current increased the size of the inhibition zone.

Copper also shows antimicrobial properties, both in the ionic form and the uncharged metallic form, as summarized in Table 1. In the uncharged form copper showed bactericidal properties against *E. faecalis*. A minimal current produced bactericidal results for all Gram (+) species of bacteria, and higher currents produced larger zones. Copper did not have an effect on Gram (−) bacterial species at currents used.

Surprisingly, cadmium results are unique in producing antimicrobial effects against all organisms tested, and the pattern of efficiency held true both in the absence and presence of electrical stimulation. Increasing the current resulted in minimal changes in microbial response. Cadmium produced a double zone of inhibition: an inner zone of complete clearing closer to the wire, and an outer zone of decreased bacterial growth (incomplete clearing). For descriptive purposes, the inner zone is considered to be "microbiocidal", while the outer zone is considered "microbistatic", or inhibitory. Numbers shown in Table 1 reflect this double zone of inhibition such that the size of the "inner zone" is present first and the size of the "outer zone" is presented in parentheses. Additionally, cadmium consistently showed some inhibitory effect in the absence of electrical charge; increasing the current had little additional effect.

TABLE 1

| Current | Gram Positive | | | Gram Negative | | Fungus |
|---|---|---|---|---|---|---|
| | S. aureus | E. faecalis | MRSA | E. coli | P. aeruginosa | C. albicans |
| Silver | | | | | | |
| 0 µA | 6 | 0 | 0 | 5 | 0 | 0 |
| 0.5 µA | 18 | 17 | 18 | 20 | 18 | 34 |
| 1 µA | 20 | 19 | 18 | 21 | 21 | 30 |
| 10 µA | 20 | 21 | 18 | 25 | 21 | 32 |
| 20 µA | 20 | 20 | 18 | 24 | 20 | 30 |
| Gold | | | | | | |
| 0 µA | 3 | 0 | 0 | 0 | 0 | 0 |
| 0.5 µA | 0 | 0 | 0 | 0 | 0 | 0 |
| 1 µA | 0 | 0 | 0 | 10 | 0 | 0 |
| 10 µA | 0 | 0 | 0 | 0 | 0 | 0 |
| 20 µA | 0 | 0 | 0 | 0 | 0 | 0 |
| Titanium | | | | | | |
| 0 µA | 0 | 0 | 0 | 0 | 0 | 0 |
| 0.5 µA | 0 | 0 | 0 | 0 | 0 | 0 |
| 1 µA | 0 | 0 | 0 | 0 | 0 | 0 |
| 10 µA | 0 | 0 | 0 | 0 | 0 | 0 |
| 20 µA | 0 | 0 | 0 | 0 | 0 | 0 |
| Copper | | | | | | |
| 0 µA | 0 | 11 | 0 | 0 | 0 | 0 |
| 0.5 µA | 14 | 16 | 7 | 0 | 0 | 0 |
| 1 µA | 6 | 16 | 6 | 0 | 0 | 0 |
| 10 µA | 0 | 15 | 9 | 0 | 0 | 0 |
| 20 µA | 8 | 18 | 11 | 0 | 0 | 0 |
| Stainless steel | | | | | | |
| 0 µA | 0 | 0 | 0 | 0 | 0 | 0 |
| 0.5 µA | 0 | 0 | 0 | 0 | 0 | 0 |
| 1 µA | 0 | 0 | 0 | 0 | 0 | 0 |
| 10 µA | 0 | 0 | 0 | 0 | 0 | 0 |
| 20 µA | 0 | 0 | 0 | 0 | 0 | 0 |
| Cadmium | | | | | | |
| 0 µA | 8 (15) | 5 | 14 | 6 (18) | (17) | 28 |
| 0.5 µA | 6 (10) | 6 | 13 | 5 (18) | (12) | 28 |
| 1 µA | 8 (15) | 6 | 13 | 4 (18) | (18) | 31 |
| 10 µA | 6 (14) | 5 | 15 | 6 (18) | (16) | 30 |
| 20 µA | 7 (15) | 5 | 16 | 5 (17) | (18) | 30 |
| Zinc | | | | | | |
| 0 µA | 0 | 0 | 0 | 0 | 0 | 0 |
| 0.5 µA | 0 | 0 | 0 | 0 | 0 | 0 |
| 1 µA | 0 | 0 | 0 | 0 | 0 | 0 |
| 10 µA | 0 | 0 | 0 | 0 | 0 | 0 |
| 20 µA | 0 | 0 | 0 | 0 | 0 | 0 |
| Nickel | | | | | | |
| 0 µA | 0 | 0 | 0 | 0 | 0 | 0 |
| 0.5 µA | 0 | 0 | 0 | 0 | 0 | 0 |
| 1 µA | 0 | 0 | 0 | 0 | 0 | 0 |
| 10 µA | 0 | 0 | 0 | 0 | 0 | 0 |
| 20 µA | 0 | 0 | 0 | 0 | 0 | 0 |

Example 2

Characterization of Effective Antimicrobial Metals

A "killing curve analysis" may be performed in order to characterize parameters which achieve an antimicrobial effect. A predetermined number of colony forming units/ml (CFU/ml), established in a growth medium, are transferred to a saline solution and then exposed to the antimicrobial metal or metal form. At predetermined time intervals, an aliquot is removed, diluted (if necessary), inoculated onto blood agar plates and incubated overnight at 37° C. The resulting growth is quantified as CFU/ml. A graph, with time as the X-axis and CFU/ml as the Y-axis demonstrates the point at which the antimicrobial effect and microbial population growth intersect. The concentration of metal required for antimicrobial effect can be determined by examining the time point at which the microbial population begins to decrease.

To examine the rate of diffusion of ions away from the metal source, i.e. the rate at which the microbes are inhibited from growing (or killed), high performance microscopy may be used. A high performance microscopic system developed by Cytoviva allows for real-time observation of living cells and cellular components without the use of staining agents. By observing the microbial response to a given metal, a "velocity" of microbial destruction can be directly observed. The rate of diffusion of ions through agar can be inferred from the velocity of kill.

In this example, silver is tested with respect to two different bacterial species, $E.\ coli$ and $S.\ aureus$. A current of 0.5 µA is used in this example.

Strains of $E.\ coli$ and $S.\ aureus$ isolated from samples submitted to the Pennsylvania State University Animal Diagnostic Laboratory, are separately diluted to a 0.5 MacFarland standard and added to individual test tubes containing 10 mls of sterile Tryptic Soy Broth (TSB). A silver wire (99.97% purity) having a uniform diameter of 1.0 mm served as a source of ions.

Two small holes are burned into the screw cap of each test tube. Silver Wires (99.97% purity), having uniform diameters of 1.0 mm, served as ion sources. The wires are aseptically threaded through the screw cap holes and positioned to expose a total length of 32 mm into the previously inoculated TSB. This resulted in the exposure of 1 $cm^2$ of silver wire to growing bacterial cells. Electrical current is generated by placing a standard 1.55 Volt AA battery in series with a 3.01 MΩ resistor. The current that is generated by the 3.01 MΩ resistor is 0.5 µA when combined into the circuit. Additionally a circuit, formed without any resistor is utilized and inserted into a tube in an identical fashion. The circuits are completed by aseptically threading the anode through another hole in the test tube screw cap and into the TSB. One tube of each bacterial species, serves as the control. It contained a silver wire, but no external circuit is connected. The silver wire as well as the anode wire is placed in contact with the bacterially laden broth continued within the test tube. This setup is used to produce "killing curves".

The tubes are incubated in air at room temperature for a total of 8 hours. Every hour the test tube is vortexed for approximately 10 seconds. The test tube cap is then opened and a 10 µl sample of broth is aseptically drawn from the test tube. The test tube are again closed and vortexed. The sample is plated onto blood agar plates using a spiral plating technique. The blood agar plates are incubated at room temperature for 24 hours. The number of colonies present on the blood agar plates at 24 hours are counted and recorded.

Figure 3:
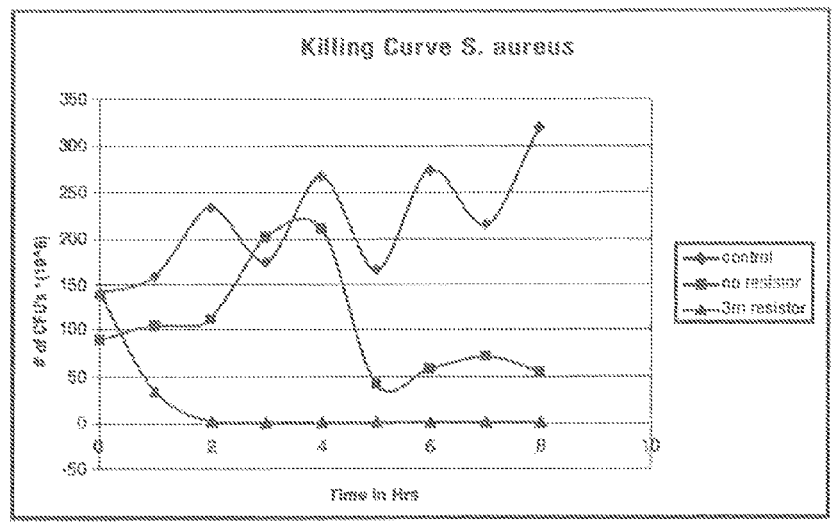
FIG. 3 is a "killing curve" showing the killing rate of an embodiment of the present invention associated with *S. aureus*.

The results clearly demonstrate that the charged form of the silver metal has a much greater kill rate when compared to the non-charged material. A "killing curve" shown in FIG. 3 shows the killing rate associated with $S.\ aureus$. The results clearly demonstrate a bacterial reduction rate of approximately $5.698*10E12$ bacteria per hour. Within this time frame both the control and the silver with no resistor allow bacterial growth.

Figure 4:
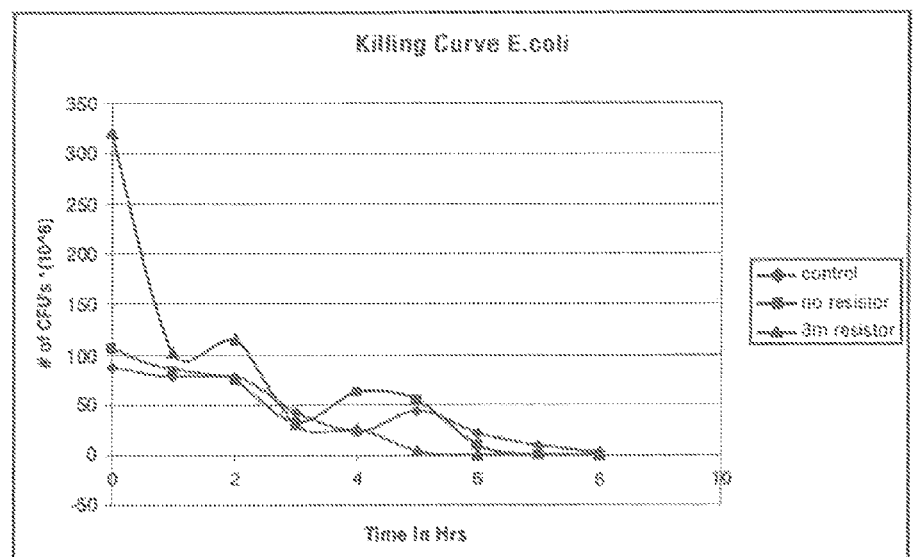
FIG. 4 is a "killing curve" showing the killing rate of an embodiment of the present invention for *Escherichia coli*.

A "killing curve" for $Escherichia\ coli$ in FIG. 4 shows the killing rate associated with $E.\ coli$. The 3 MΩ resistor utilized in this circuit corresponds to the smallest current 0.5 µA. The curve shows bacterial reduction from $320*10E6$ to zero within five hours, a rate of approximately $72*10E6$ bacteria per hour. Within this time period both the control and the silver with no resistor tests continue to support bacterial growth.

Example 3

Optimization of Critical Operational Parameters of Antimicrobial Metals

Antimicrobial properties of specific metals or metal forms differ when modifications are made in the experimental parameters. Using data from the "killing curve analyses", critical parameters will be established for the generation of optimal antimicrobial effects, and can then be balanced against the characteristics of the application into which the metal will be incorporated.

In order to evaluate any possible toxicity of antimicrobial metal compositions on mammalian cells, in vitro cell culture systems may be utilized. Specifically, batteries and resistors connected in series with a predetermined antimicrobial metal composition is aseptically threaded into a mammalian cell culture flask and allowed to run, generating metal ions within the culture. Cells are monitored during testing for morphological changes and percentages of live vs. dead cells. In addition, treated and control cells may be evaluated via metabolic function assays such as albumin and urea levels in hepatocytes; bone alkaline phosphatase levels in osteoblasts; and matrix protein levels in chrondrocytes.

In addition, the effects of circuit polarity, operation time and duty cycle are evaluated on cells in vitro using device parameters and optimized for maximal antimicrobial effect and low toxicity. An external circuit is constructed allowing for varying run-time cycles and alternating circuit polarities. The external circuit with battery, resistor, an inverter for reversing polarity, and a timer will be connected in series with the test antimicrobial metal. The circuit will be aseptically threaded into the cell culture flask and allowed to run, generating antimicrobial ions within the culture. The continuous running time of the circuit as well as the polarity of the circuit will be manipulated by varying the circuit timer and changing the polarity of the circuit via the switch.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

What is claimed is:

1. An antimicrobial device, comprising:
a device body having a first element including a plurality of first external surfaces and a second element including a plurality of second external surfaces, at least one of the first and second elements including an antimicrobial material, wherein the first and second external surfaces are adjacent to and directly facing one another in more than one location, wherein each of the adjacent first and second external surfaces are separated from one another by a space, and wherein the first element and second element remain free from contact with one another;
one or more insulators configured to electrically decouple the first and second elements from each other, said one or more insulators being positioned in the spaces directly between each of the adjacent first and second external surfaces of the first and second elements; and
an electrical power supply configured to apply electric potential across the first and second elements;
wherein said first and second elements are configured to be electrically coupled together by an object that comes into contact with said device body causing electrical current to flow between said first and second elements and causing emission of antimicrobial ions from the antimicrobial material toward the object.

2. The device of claim 1, wherein the antimicrobial material is a metal-containing coating and is disposed on the external surface of at least one of the elements.

3. The device of claim 1, wherein the antimicrobial material comprises at least one of silver, copper, cadmium, gold, zinc, cobalt, nickel, palladium, manganese, chromium, an ionic form, an alloy, a composite, a mixture, a combination of silver and copper, a combination of silver and cadmium, a combination of copper and cadmium, and a combination of silver, cadmium, and copper, and wherein the ratio between any two metals included in the antimicrobial material ranges from about 1000:1 to 1:1000.

4. The device of claim 2, wherein the metal-containing coating is disposed in a pattern that includes interlocking stripes defining discontinuous regions of coating, wherein the distance between discontinuous regions of coating is selected to account for the diffusion distance of ions generated from the coating.

5. The device of claim 1, wherein the one or more insulators are at least partially enclosed within the device body.

6. The device of claim 1, wherein the antimicrobial material contains metal and is formed of at least one of a wire, paint, ribbon, mesh, lattice, sheet, plate, and foil.

7. The device of claim 6, wherein the antimicrobial material is attached to the at least one of the first and second elements with at least one of welding and an adhesive.

8. The device of claim 1, wherein the antimicrobial material is non-uniformly disposed on the at least one of the first and second elements.

9. The device of claim 2, wherein the metal-containing coating has a thickness of about $1\times10^{-9}$-$5\times10^{-3}$ meters.

10. The device of claim 1, wherein the one or more insulators have a resistive value greater than a resistive value of an object that comes into contact with said device body causing electrical current to flow between said first and second elements and causing emission of antimicrobial ions from the antimicrobial material toward the object.

11. The device of claim 1, wherein the device body is configured for incorporation within at least one of a textile, a filter, an item of medical equipment, an electronic device, an item of processing equipment for a consumable, a ventilation system component, a food preparation surface, a laboratory surface, a household surface, a personal care accessory, a hardware surface, and a surface configured for human or animal interaction.

12. The device of claim 1, wherein said first and second elements are configured to be electrically connected to one another by at least one of a human tissue, one or more microbes, a fluid, environmental humidity, a textile, and a food item.

13. The device of claim 1, wherein each of the first and second elements, the one or more insulators, and the power supply are fixed in place relative to one another prior to an object coming into contact with said device body.

14. An antimicrobial device, comprising:
a device body having a first element including a plurality of first external surfaces and a second element including a plurality of second external surfaces, wherein the first and second external surfaces are adjacent to and directly facing one another in more than one location, wherein each of the adjacent first and second external surfaces are separated from one another by a space, and wherein the first element and second element remain free from contact with one another;
a first metal component containing an antimicrobial metal disposed on the first element;
a power source having a first terminal in connection with the first element and a second terminal in connection with the second element; and
one or more electrical insulators existing in a current path between the first terminal and the second terminal, said one or more insulators being synthetic or air or both and being positioned in the spaces directly between each of the adjacent first and second external surfaces of the first and second elements;
wherein said first and second elements are configured to be electrically coupled together by an object that comes into contact with said device body, and wherein each of the first and second components, the one or more insulators, and the power source are fixed in place relative to one another prior to the object coming into contact with said device body.

15. The device of claim 14, wherein the one or more insulators are configured to be sandwiched between the first and second elements.

16. The device of claim 14, wherein a neutral or negatively charged object with respect to the first metal component which comes into contact with the first metal component causes an electric potential between the first metal component and the second element.

17. The device of claim 14, wherein the first metal component is a metal-containing coating.

* * * * *